(12) United States Patent
Zhang et al.

(10) Patent No.: US 9,991,448 B2
(45) Date of Patent: Jun. 5, 2018

(54) COMPOUND, LUMINESCENT MATERIAL AND ORGANIC LIGHT EMITTING DEVICE USING SAME

(71) Applicants: SHANGHAI TIANMA AM-OLED CO., LTD., Shanghai (CN); TIANMA MICRO-ELECTRONICS CO., LTD., Shenzhen (CN)

(72) Inventors: Zhengchuan Zhang, Shanghai (CN); Hao Dai, Shanghai (CN); Defeng Bi, Shanghai (CN)

(73) Assignees: SHANGHAI TIANMA AM-OLED CO., LTD., Shanghai (CN); TIANMA MICRO-ELECTRONICS CO., LTD., Shenzhen (CN)

( * ) Notice: Subject to any disclaimer, the term of this patent is extended or adjusted under 35 U.S.C. 154(b) by 0 days. days.

(21) Appl. No.: 15/204,661

(22) Filed: Jul. 7, 2016

(65) Prior Publication Data

US 2017/0288150 A1    Oct. 5, 2017

(30) Foreign Application Priority Data

Apr. 5, 2016    (CN) .......................... 2016 1 0206654

(51) Int. Cl.
*H01L 51/00* (2006.01)
*C07D 471/20* (2006.01)
(Continued)

(52) U.S. Cl.
CPC ........ *H01L 51/0072* (2013.01); *C07D 471/10* (2013.01); *C07D 471/20* (2013.01);
(Continued)

(58) Field of Classification Search
None
See application file for complete search history.

(56) References Cited

U.S. PATENT DOCUMENTS

| | | | |
|---|---|---|---|
| 6,251,531 B1 * | 6/2001 | Enokida | ................ C07C 211/61 313/504 |
| 2012/0091448 A1 * | 4/2012 | Ueno | .................... H01L 51/506 257/40 |

FOREIGN PATENT DOCUMENTS

| CN | 103232843 A | 8/2013 |
|---|---|---|
| CN | 10369422 A | 4/2014 |

(Continued)

OTHER PUBLICATIONS

Machine English translation of Lee et al. (KR 10-2014-0076522). Aug. 1, 2017.*

(Continued)

*Primary Examiner* — J. L. Yang
(74) *Attorney, Agent, or Firm* — Kilpatrick Townsend & Stockton LLP

(57) ABSTRACT

The present invention discloses a compound represented by the following Formula I, and a luminescent material and an organic light emitting device using the same. Said com- (Continued)

pound has a characteristic of thermally activated delayed fluorescence, and can be used in luminescent materials and in organic light emitting devices.

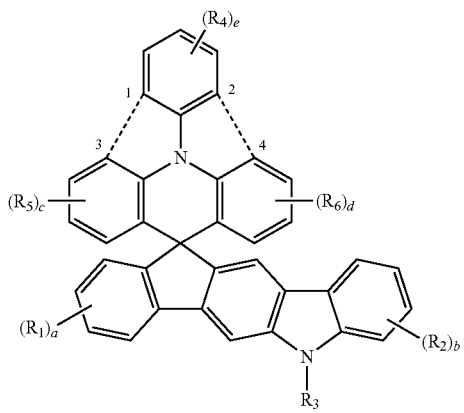

Formula I

(51) Int. Cl.
C09K 11/06 (2006.01)
C07D 471/10 (2006.01)
H01L 51/50 (2006.01)
C09K 11/02 (2006.01)

(52) U.S. Cl.
CPC ............ *C09K 11/025* (2013.01); *C09K 11/06* (2013.01); *H01L 51/0058* (2013.01); *H01L 51/0065* (2013.01); *H01L 51/0067* (2013.01); *H01L 51/5004* (2013.01); *H01L 51/5012* (2013.01); *H01L 51/5028* (2013.01); *H01L 2251/552* (2013.01)

(56) References Cited

FOREIGN PATENT DOCUMENTS

| KR | 10-2014-0076522 | * | 6/2014 |
| KR | 20140076552 A | | 6/2014 |
| KR | 20140120420 A | | 10/2014 |

OTHER PUBLICATIONS

The first Office Action in the corresponding Chinese application CN201610206654.9 dated Apr. 6, 2017.

9 Claims, 6 Drawing Sheets

\* cited by examiner

HOMO
5a

LUMO
5b

COMPOUND, LUMINESCENT MATERIAL AND ORGANIC LIGHT EMITTING DEVICE USING SAME

CROSS-REFERENCE TO RELATED APPLICATIONS

This application is based upon and claims priority to Chinese Patent Application No. 201610206654.9, filed on Apr. 5, 2016, the entire contents of which are incorporated herein by reference.

TECHNICAL FIELD

The present invention belongs to the technical field of organic luminescence, and particularly relates to a thermally activated delayed fluorescent compound and a luminescent material and an organic light emitting device using the same.

BACKGROUND

Organic light emitting devices (OLEDs) are thin-film light emitting devices made from organic semiconductive materials and driven by direct current voltage.

Simply speaking, the light emitting mechanism of OLEDs is as follows: electrons and holes, driven by a certain voltage, are injected into the electron transporting layer and the hole transporting layer, respectively, from the cathode and the anode; electrons and holes meet each other to form excitons (generally classified as singlet excitons and triplet excitons), which excites the luminescent molecules in the luminescent material to emit visible lights.

Conventional organic fluorescent materials can utilize only 25% of electrically excited singlet excitons to emit light, leading to low internal quantum efficiency of the device (25% at most). Phosphorescent material has enhanced intersystem crossing due to strong spin-orbit coupling of heavy atom center, and can effectively utilize singlet excitons and triplet excitons formed by electrical excitation to emit light, and theoretically may make the device to reach an internal quantum efficiency of 100%. However, phosphorescent materials contain heavy metals, and have disadvantages such as high costs, low stability of the material, low efficacy of the device, which limit the applications thereof in OLEDs.

Thermally activated delayed fluorescence (TADF, also known as E-type Delayed Fluorescence) materials are the third generation of organic luminescent materials developed after organic fluorescent materials and organic phosphorescent materials.

TADF materials normally have small singlet-triplet energy level difference ($\Delta E_{ST}$), so that triplet excitons can be converted to singlet excitons through reverse intersystem crossing (RISC) to emit light. Therefore, TADF materials can sufficiently utilize singlet excitons and triplet excitons formed by electrical excitation to emit light, and theoretically may also make the device to reach an internal quantum efficiency of 100%. In addition, due to RISC, the lifetime of the light produced by this type of materials is longer than that of traditional fluorescence or phosphorescence. Furthermore, TADF materials have controllable structures, stable properties, low prices, and are free of precious metals, and therefore have broad prospect of being used in the field of OLEDs.

The current studies on TADF materials are focused on how to lower the singlet-triplet energy level difference $\Delta E_{ST}$ to a value which meets the requirement of RISC. Theoretically, when $\Delta E_{ST} \leq 0.2$ eV, RISC can be realized.

Upon research, it has been found that there is a positive correlation between $\Delta E_{ST}$ and the degree of orbital overlap between HOMO and LUMO, wherein HOMO refers to highest occupied molecular orbital, and LUMO refers to lowest unoccupied molecular orbital. If $\Delta E_{ST}$ needs to be lowered, this may be achieved by separating HOMO from LUMO as much as possible while ensuring the recombination of excitons.

Currently, there lacks research on the chemical structures, optical properties and physical properties of TADF materials and the correlation thereof with OLEDs, which limits the development of new TADF materials, leading to lacking of variety of current TADF materials, which cannot meet the current requirements on the development of OLEDs.

SUMMARY

In one aspect, the present invention provides a compound represented by the following Formula I,

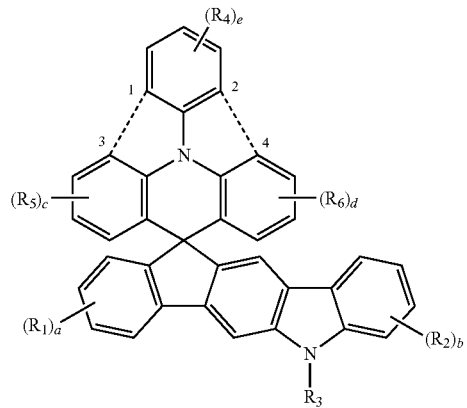

Formula I in Formula I, $R_1$ and $R_2$ are each independently hydrogen, halogen, trifluoromethyl, nitro or cyano, or have a structure of $(R_7)_f—R_8—$, a structure of

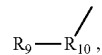

or a structure of

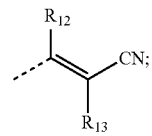

wherein, in the structure of $(R_7)_f—R_8—$, $R_8$ is C6~C34 aryl or C3~C34 nitrogen-containing heteroaryl, and $R_7$ is hydrogen, halogen, trifluoromethyl, nitro or cyano, and f is an integer greater than or equal to 1;

in the structure of

$R_{10}$ is

and $R_9$ is C1~C8 alkyl, C6~C12 aryl; or
$R_{10}$ is

and $R_9$ is C6~C12 aryl; or
$R_{10}$ is

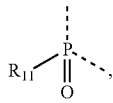

and $R_9$ and $R_{11}$ are each independently C6~C12 aryl;
in the structure of

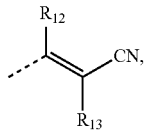

$R_{12}$ and $R_{13}$ are each independently hydrogen, C1~C8 alkyl, C6~C12 aryl;

$R_3$ has a structure of the above $(R_7)_f$—$R_8$—;

$R_4$, $R_5$ and $R_6$ are each independently hydrogen, C1~C8 alkyl or heteroalkyl, C6~C8 aryl or C4~C8 heteroaryl;

in Formula I, the dashed line between the carbon atoms at position 1 and position 3 represents that a C—C bond may be present or not present between the two carbon atoms;

in Formula I, the dashed line between the carbon atoms at position 2 and position 4 represents that a C—C bond may be present or not present between the two carbon atoms;

in Formula I, a and b are each independently an integer of 1~4, c, d and e are each independently an integer of 1~3.

In another aspect, the present invention provides a luminescent material, comprising the compound represented by the above Formula I.

In another aspect, the present invention provides an organic light emitting device, comprising:
a substrate;
a first electrode disposed on the substrate;
a second electrode disposed opposite to the first electrode; and
an organic functional layer disposed between the first electrode and the second electrode, the organic functional layer comprising one or more organic material layers, and at least one of the organic material layers being a light emitting layer; and, wherein
at least one of the organic material layers in the organic functional layer comprises the compound represented by the above Formula I.

The compound of the present invention represented by Formula I has a characteristic of thermally activated delayed fluorescence, and can be used in luminescent materials and in organic light emitting devices.

BRIEF DESCRIPTION OF THE DRAWINGS

FIGS. 2a, 2b and 2c show the orbit distributions of Compound 1 obtained in Example 1 of the present invention, wherein FIG. 2a shows the distribution of HOMO; FIG. 2b shows the distribution of coexistence of HOMO and LUMO; and FIG. 2c shows the distribution of LUMO;

FIGS. 4a and 4b show the orbit distributions of Compound 2 obtained in Example 2 of the present invention, wherein FIG. 4a shows the distribution of HOMO; and FIG. 4b shows the distribution of LUMO;

FIGS. 5a and 5b show the orbit distributions of Compound 4 obtained in Example 3 of the present invention, wherein FIG. 5a shows the distribution of HOMO; and FIG. 5b shows the distribution of LUMO; and FIGS. 6a and 6b show the orbit distributions of Compound 5 obtained in Example 4 of the present invention, wherein FIG. 6a shows the distribution of HOMO; and FIG. 6b shows the distribution of LUMO.

DETAILED DESCRIPTION

Figure 1:
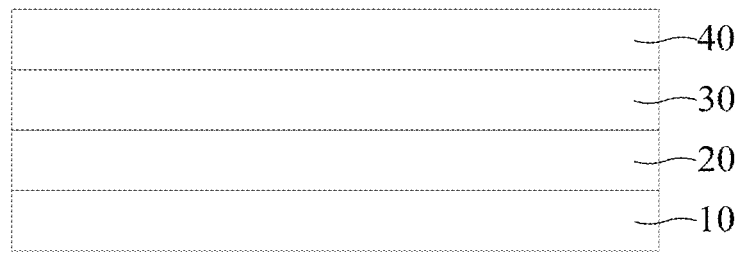
FIG. 1 is a scheme of the structure of an organic light emitting device according to one specific embodiment of the present invention.

Next, the compound of the present invention, the process for preparing said compound, the luminescent material comprising said compound, and the organic light emitting device employing said compound will be further illustrated with reference to specific embodiments.

Unless otherwise defined, all the technical terms used herein will have the same meanings as ordinarily understood by a skilled person in the relevant art to which the subject matters of the Claims pertain.

In the context of the present invention, the term "aryl" refers generally to a mono-valent group obtained by removing a hydrogen atom from a carbon in the aromatic core of an aromatic hydrocarbon molecule, including six-membered mono-cyclic aryls and fused aryls; and including substituted or unsubstituted aryls. Examples of unsubstituted aryls include, but are not limited to, phenyl, naphthyl, anthryl, phenanthryl, pyrenyl and chrysenyl.

The term "heteroaryl" refers to a mono-valent organic group obtained by replacing one or more carbon atoms in the aromatic core of an aryl with a hetero atom (e.g. O, N or S), including five- or six-membered mono-cyclic heteroaryls and fused heteroaryls, and including substituted or unsubstituted heteroaryls. Examples of unsubstituted heteroaryls include, but are not limited to, pyridyl, pyrimidyl, thienyl, furanyl, pyranyl, pyrrolyl, triazolyl, tetrazolyl, indolyl, pyridazinyl, pyrazinyl, triazinyl, quinolinyl, isoquinolinyl, thiazolyl, carbazolyl, imidazolyl, pyrazolyl, oxazolyl, oxadiazolyl, thiadiazolyl, 1,2,3-triazolyl, 1,2,4-triazolyl, benzothiazolyl, benzoxazolyl and benzimidazolyl.

The term "nitrogen-containing heteroaryl" refers to a mono-valent organic group obtained by replacing one or more carbon atoms in the aromatic core of the above aryl by a N atom.

The term "alkyl" refers to a saturated hydrocarbon group obtained by removing a hydrogen atom from an alkane molecule, including straight- or branched-chain alkyls, and including substituted or unsubstituted alkyls. Examples of alkyls include, but are not limited to, methyl, ethyl, propyl, isopropyl, isobutyl, sec-butyl, pentyl, isopentyl, hexyl.

The term "heteroalkyl" refers to a mono-valent group obtained by replacing one or more carbon atoms in the above alkyl with a hetero atom, such as O, N or S, including straight- or branched-chain heteroalkyls, including substituted or unsubstituted heteroalkyls, and including alkoxy, alkylamino, alkylsulfanyl. Examples of heteroalkyl include, but are not limited to, methoxy, ethoxy, propoxy, isopropoxy, butoxy, methylamino, ethylamino, methylsulfanyl, ethylsulfanyl, propylsulfanyl, isopropylsulfanyl, butylsulfanyl.

Examples of the term "halogen" include fluorine, chlorine, bromine, iodine.

In a specific embodiment of the present invention, it is provided a compound represented by the following Formula I:

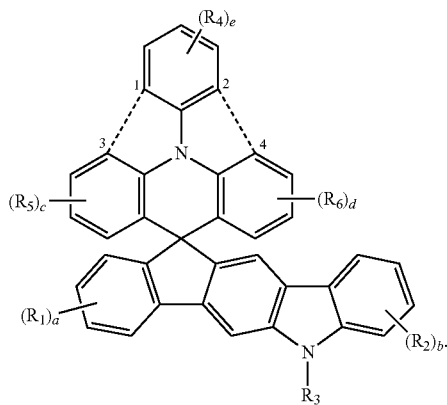

In a specific embodiment of the present invention, $R_1$ and $R_2$ are each independently hydrogen, halogen, trifluoromethyl, nitro or cyano, or have a structure of $(R_7)_f$—$R_8$—, a structure of

or a structure of

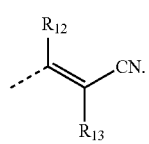

In a preferred embodiment of the present invention, $R_1$ and $R_2$ are hydrogen.

In a specific embodiment of the present invention, $R_1$, $R_2$ and $R_3$ each independently have a structure of $(R_7)_f$—$R_8$—, wherein $R_8$ is C6~C34 aryl, or C3~C34 nitrogen-containing heteroaryl, and $R_7$ is hydrogen, halogen, trifluoromethyl, nitro or cyano, and f is an integer greater than or equal to 1. Preferably, $50 \geq f \geq 1$. More preferably, f may be an integer of 1 to 6.

In a preferred embodiment of the present invention, $R_8$ is C6~C34 aryl. More preferably, $R_8$ is phenyl, biphenyl, naphthyl or fluorenyl.

In a preferred embodiment of the present invention, $R_8$ is C3~C34 nitrogen-containing heteroaryl. More preferably, $R_8$ is selected from the group consisting of pyridyl, pyrimidyl and isoquinolinyl; or $R_8$ has a structure of

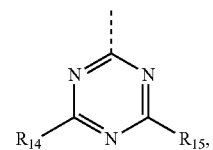

wherein $R_{14}$ and $R_{15}$ are each independently phenyl, naphthyl or anthryl.

In a more preferred embodiment of the present invention, $R_1$, $R_2$ and $R_3$ are each independently selected from the group consisting of:

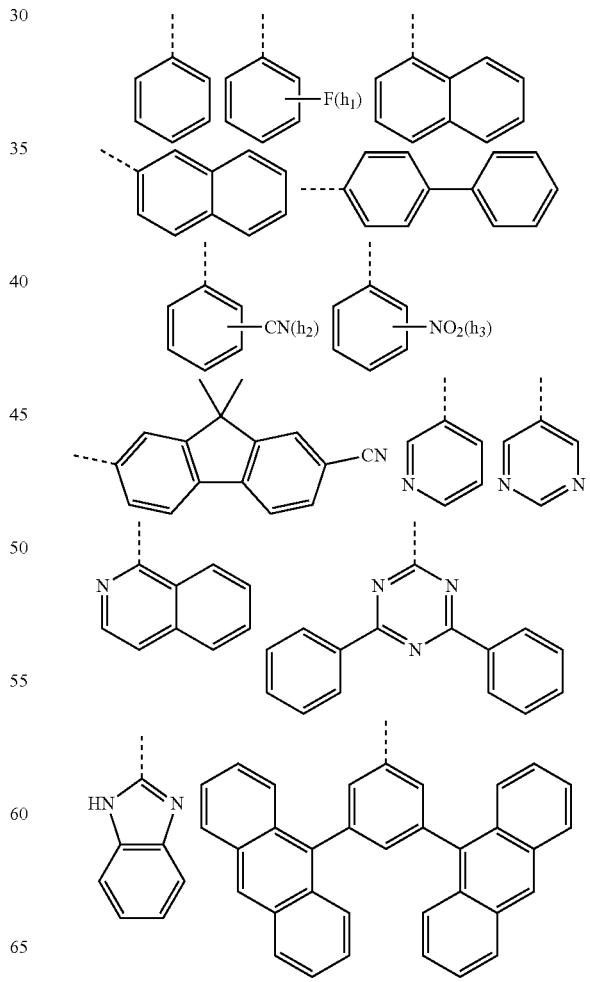

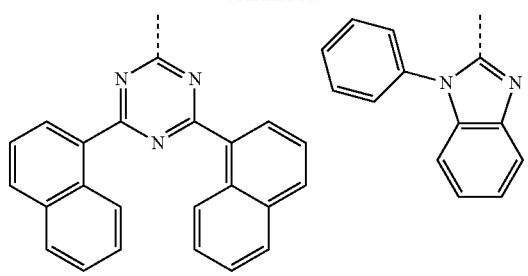
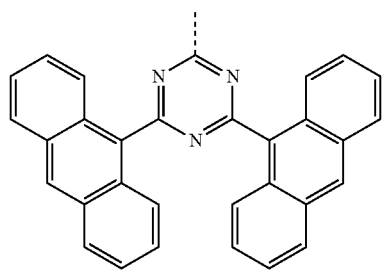
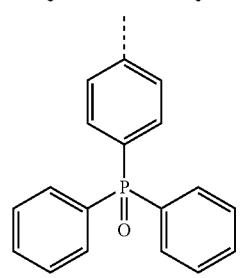
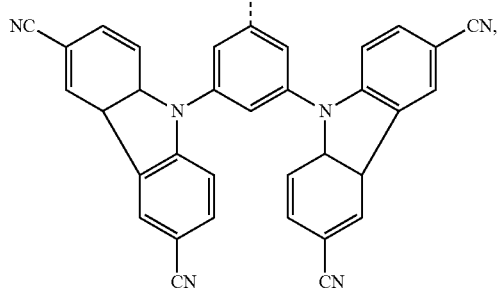

wherein $h_1$, $h_2$ and $h_3$ are each independently an integer of 1~5.

In a specific embodiment of the present invention, $R_1$ and $R_2$ each independently have a structure of

wherein $R_{10}$ is

and $R_9$ is C1~C8 alkyl, C6~C12 aryl; or $R_{10}$ is

and $R_9$ is C6~C12 aryl; or $R_{10}$ is

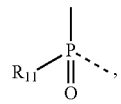

and $R_9$ and $R_{11}$ are each independently C6~C12 aryl.

In a specific embodiment of the present invention, $R_1$ and $R_2$ each independently have a structure of

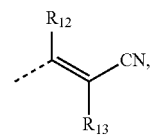

wherein $R_{12}$ and $R_{13}$ are each independently hydrogen, C1~C8 alkyl, C6~C12 aryl.

In a preferred embodiment of the present invention, $R_1$ and $R_2$ are each independently:

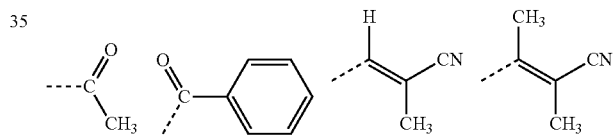

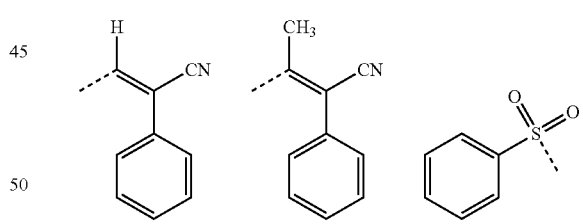

In a preferred embodiment of the present invention, at least two of the substituents $R_1$, $R_2$, $R_3$ are identical. In another preferred embodiment of the present invention, $R_1$ and $R_2$ are identical. In a further preferred embodiment of the present invention, $R_1$, $R_2$, $R_3$ are all identical.

In a specific embodiment of the present invention, in Formula I, the dashed line between the carbon atoms at position 1 and position 3 represents that a C—C bond may be present or not present between the two carbon atoms; and the dashed line between the carbon atoms at position 2 and position 4 represents that a C—C bond may be present or not present between the two carbon atoms.

In a preferred embodiment of the present invention, the compound represented by Formula I has a structure represented by any one of the following Formulae II to IV:

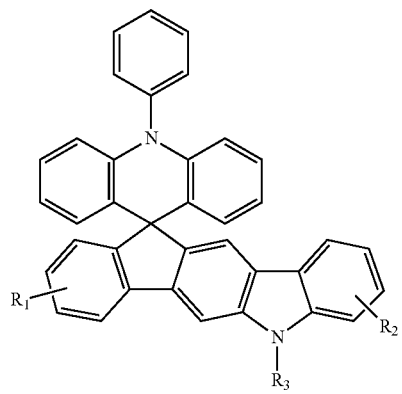

Formula II

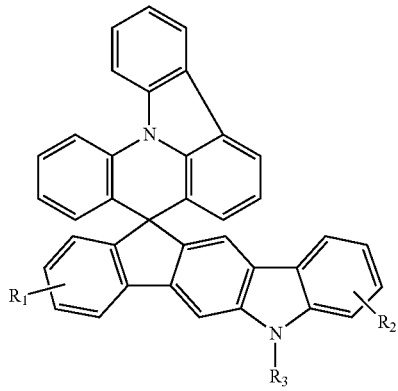

Formula III

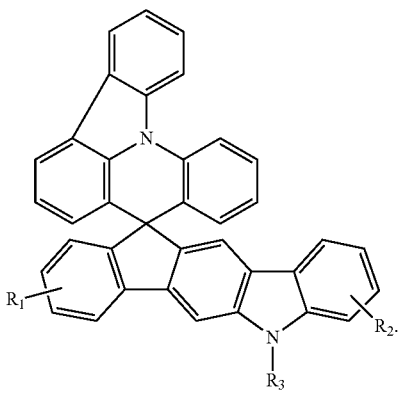

Formula IV

Specific examples of the compound represented by Formula I include, but are not limited to, the following compounds numbered 1 to 30 (wherein the compounds numbered 1, 2, 4 and 5 are Compounds 1, 2, 4 and 5 described in the following Examples 1 to 4):

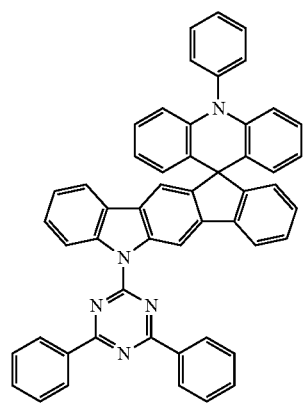

1

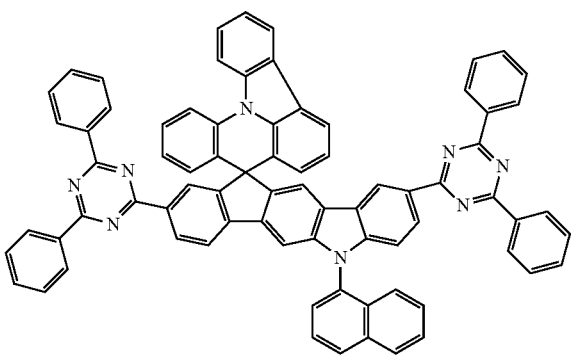

2

-continued
3
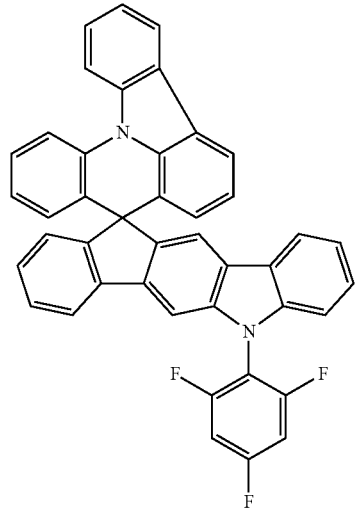
4
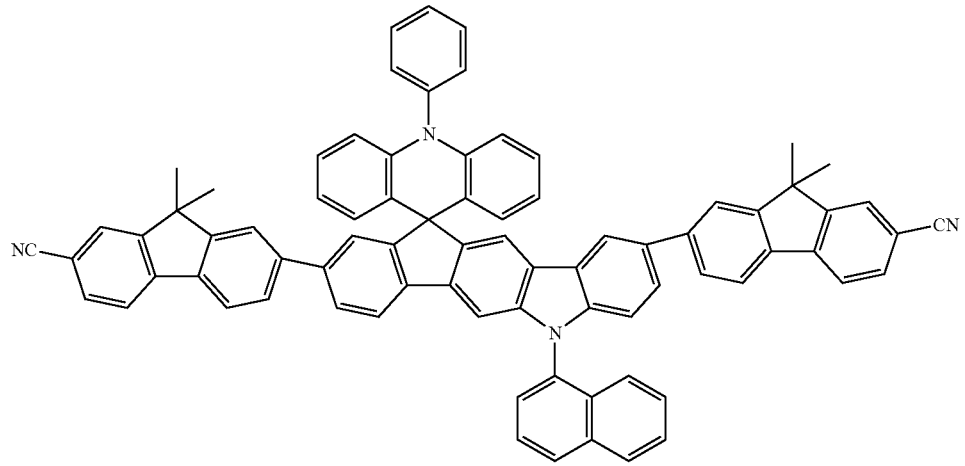
5
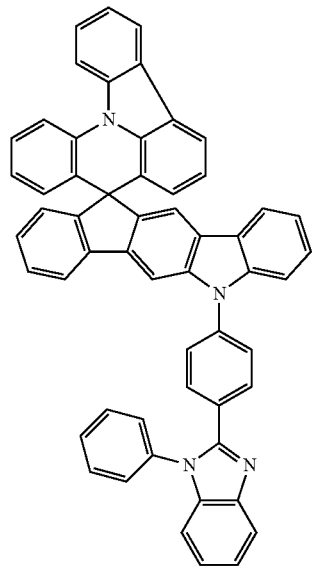
6
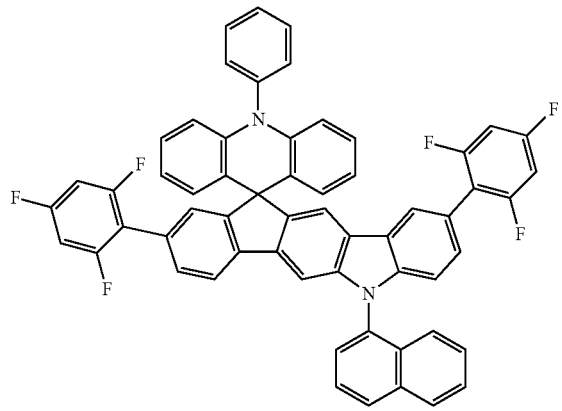

-continued
7
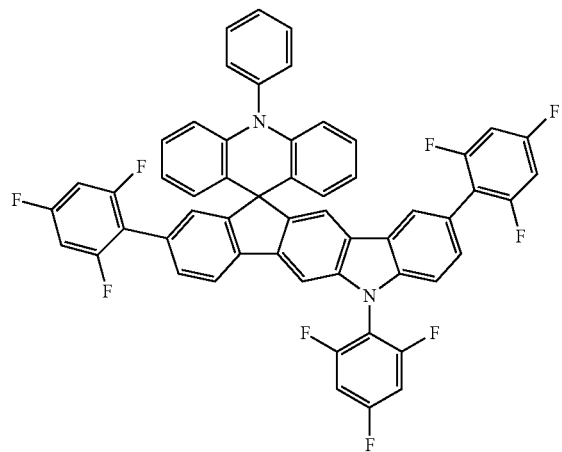
8
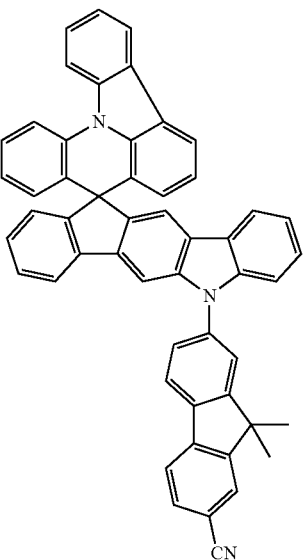
9
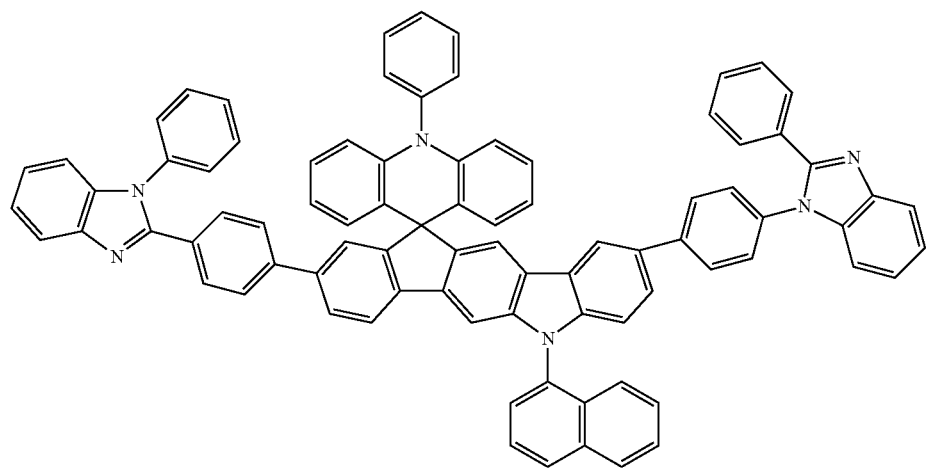
10
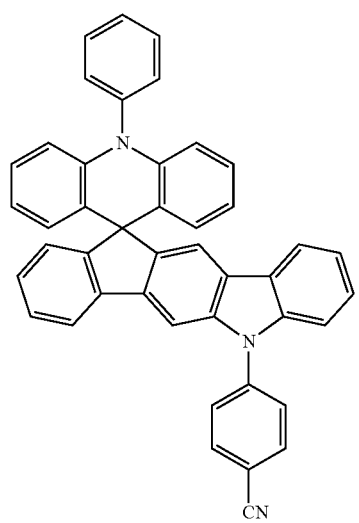

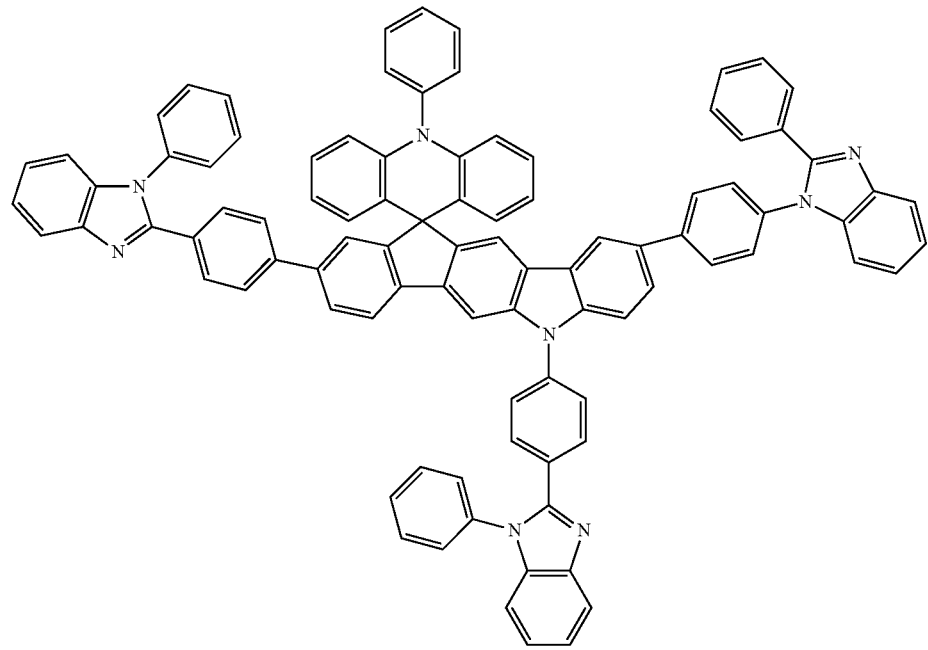
11
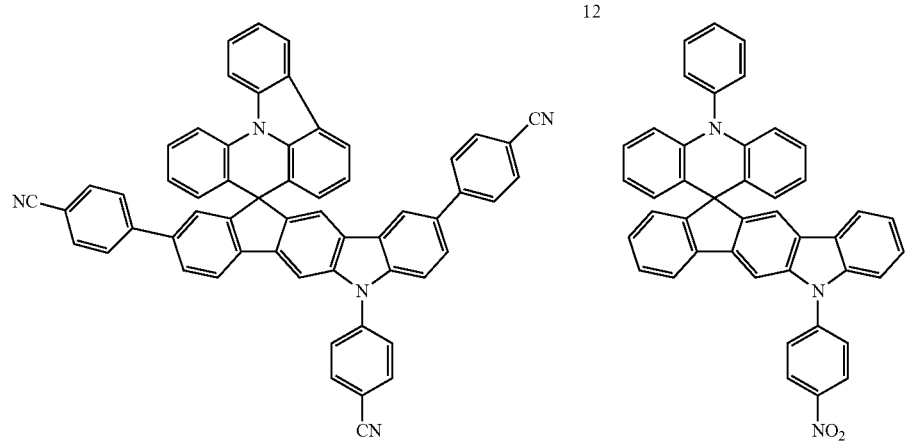
12
13
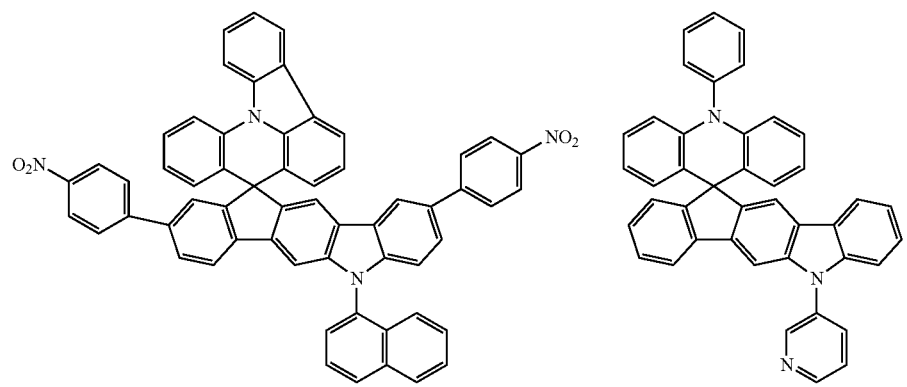
14
15

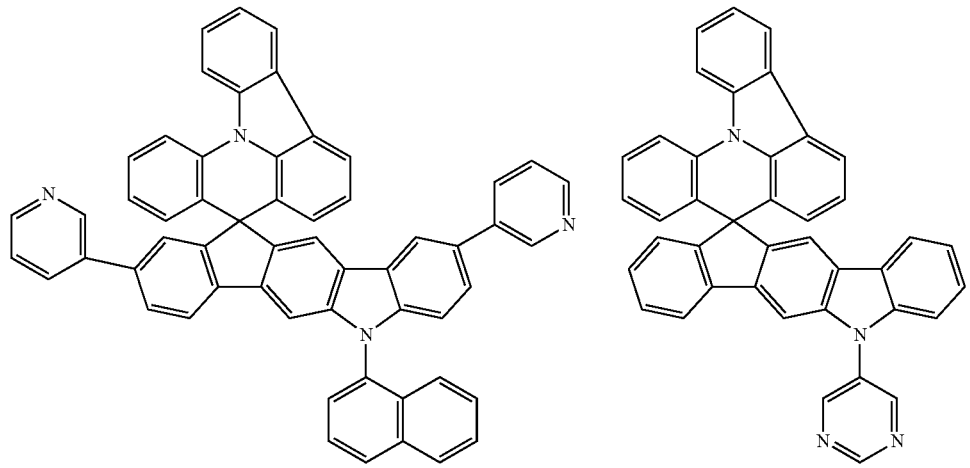
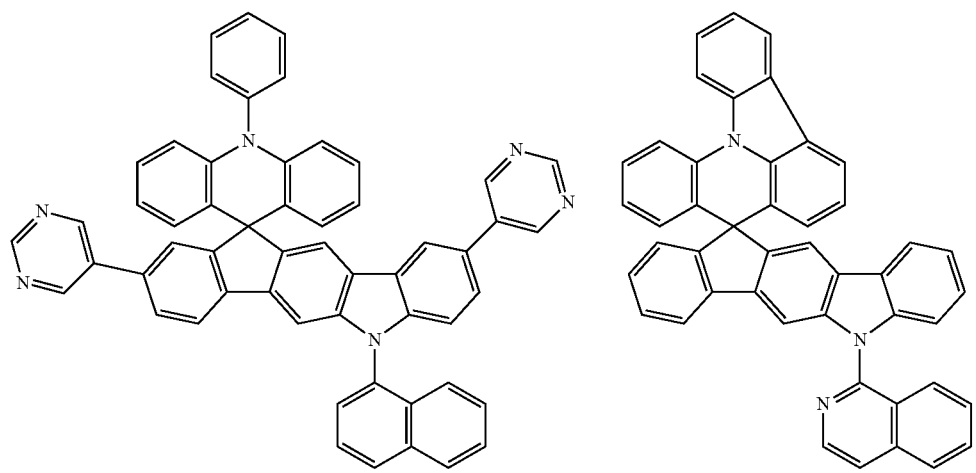
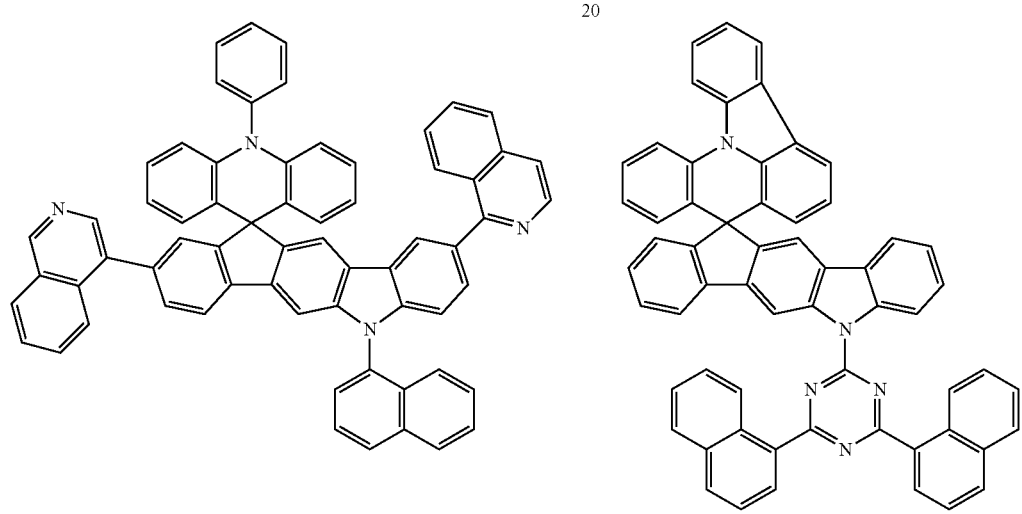

22
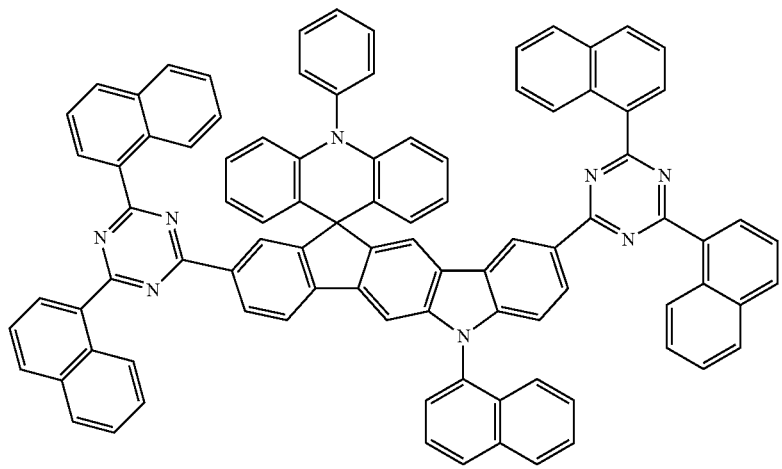
23
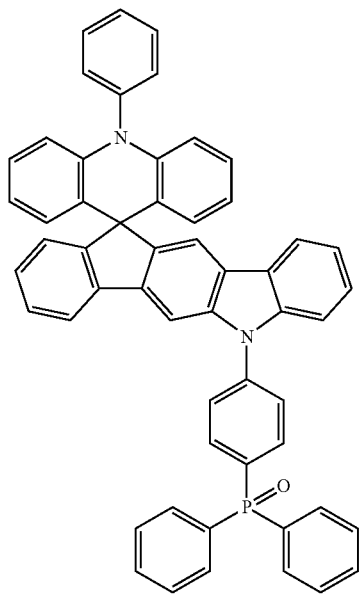
24
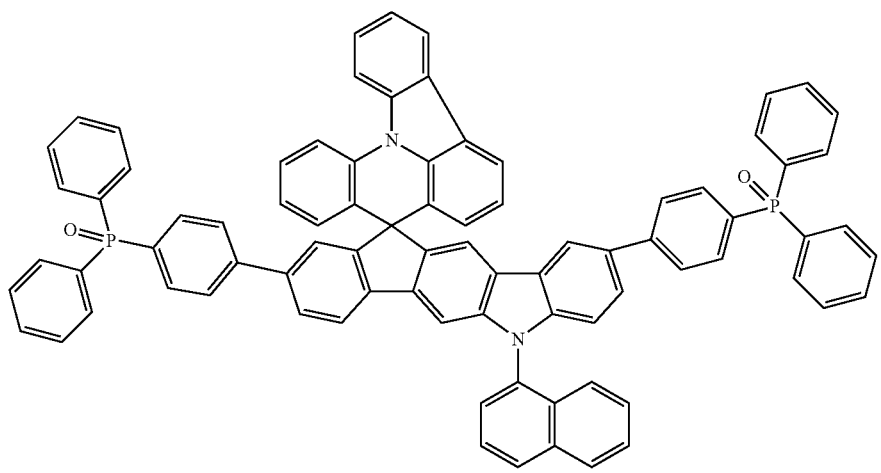

25
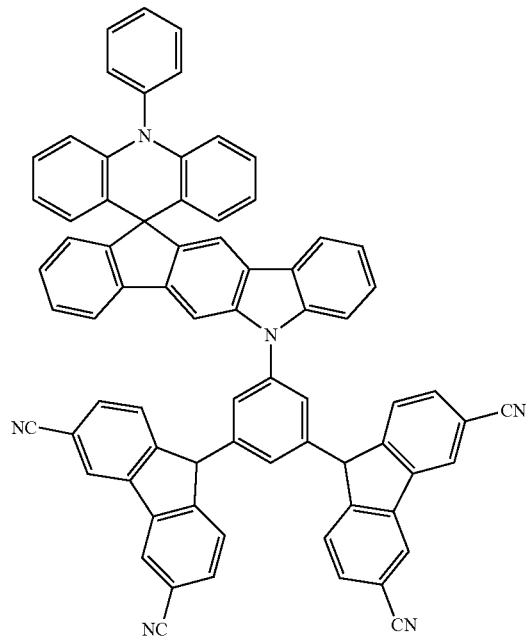
26
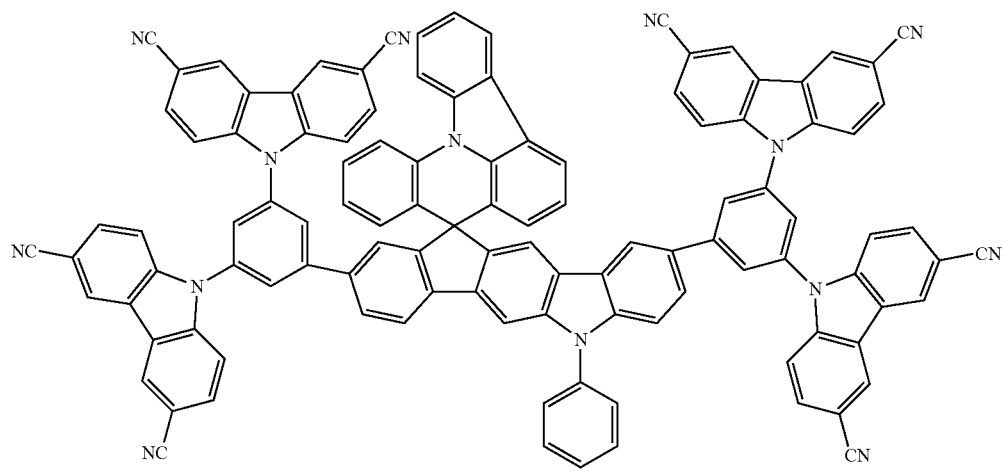
27
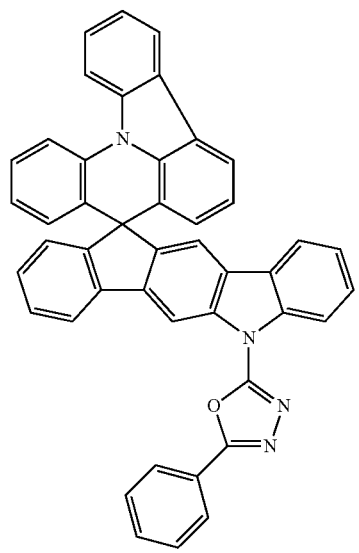

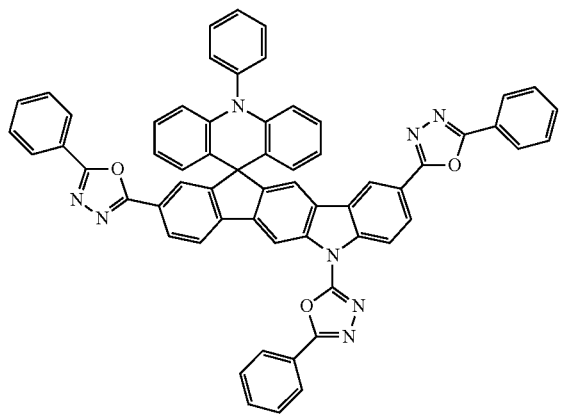

28

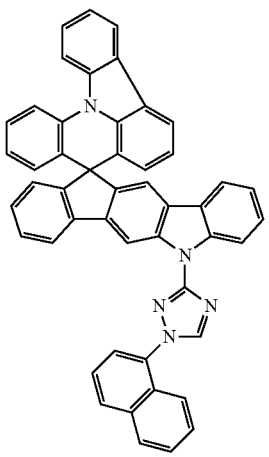

29

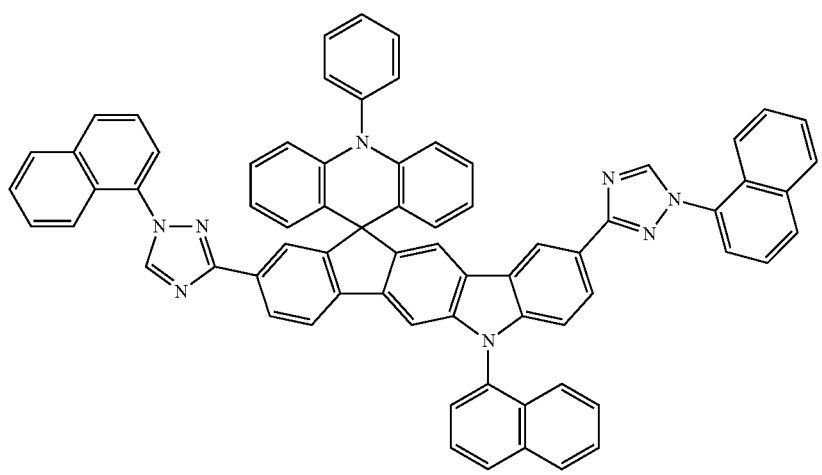

30

In another aspect, the present invention provides a luminescent material, comprising the compound represented by Formula I. In one embodiment, the luminescent material is a green fluorescent material. In another embodiment, the luminescent material is a red fluorescent material.

The compound of the present invention represented by Formula I, in addition to being used as a luminescent material, may also be used in an organic light emitting device as a luminescent material together with another organic material. For example, the compound represented by Formula I can be used as a host material in the light emitting layer, which is doped by a conventional fluorescent material as a guest material. As a host material in the light emitting layer, the compound of the present invention would significantly improve the injecting and transporting of the two carriers, and therefore improve the lifetime of the device.

When the compound represented by Formula I is used as a host material in the luminescent material, the doped guest material may be selected from the following compounds:

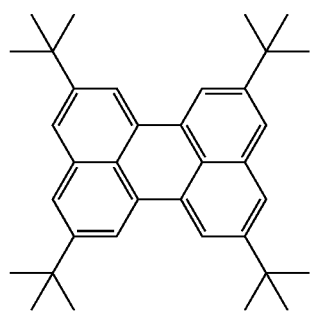

-continued

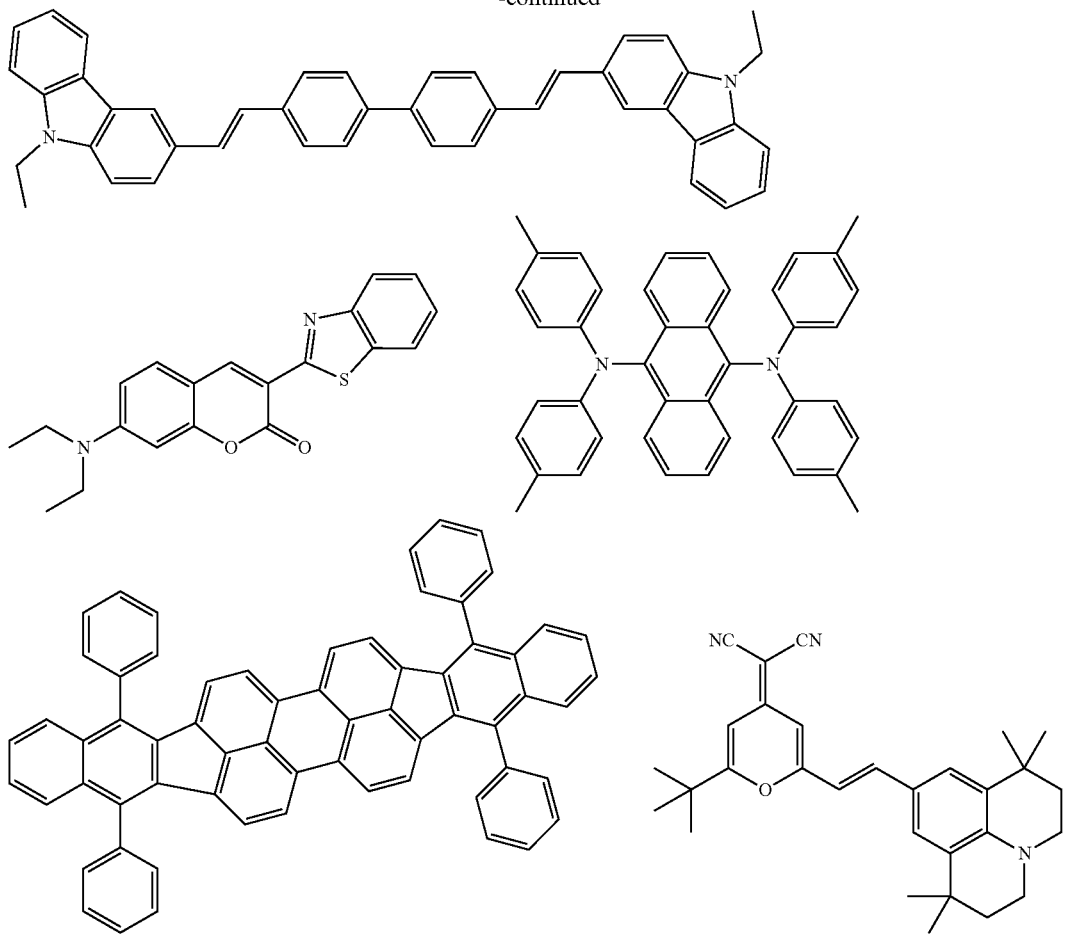

When the compound represented by Formula I is used as a guest material in the luminescent material, the host material may be selected from the following compounds:

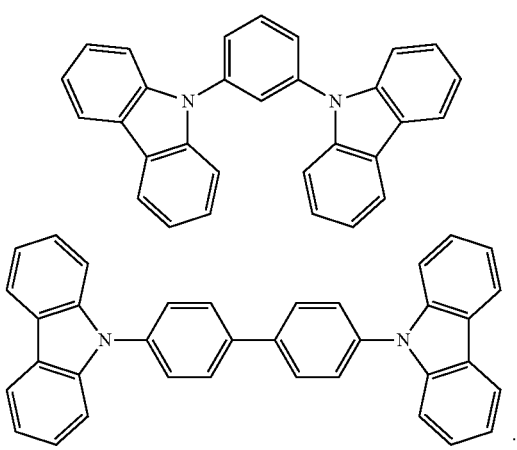

Furthermore, as shown in FIG. 1, the present invention provides an organic light emitting device, comprising a substrate 10; a first electrode 20 disposed on the substrate 10; a second electrode 40 disposed opposite to the first electrode 20; and an organic functional layer 30 disposed between the first electrode 20 and the second electrode 40.

The organic functional layer 30 comprises one or more organic material layers, and at least one of the organic material layers is a light emitting layer; wherein at least one of the organic material layers in the organic functional layer 30 comprises the compound represented by Formula I.

In a specific embodiment, the substrate 10 may be a rigid substrate or a flexible substrate. Examples of rigid substrates include, but are not limited to, glass substrate, quartz substrate, sapphire substrate, silicon substrate, metal substrate. Examples of flexible substrate include, but are not limited to, organic polymer substrate, metal oxide substrate.

In a specific embodiment, the first electrode 20 is the anode and the second electrode 40 is the cathode. Alternatively, the first electrode 20 may be the cathode, and correspondingly the second electrode 40 is the anode.

As the anode, a high work function material is generally selected, so as to inject holes smoothly into the organic functional layer 30. Examples of the anode materials include, but are not limited to, gold, silver, chromium, copper, tin indium oxide (ITO), aluminum doped zinc oxide (AZO), indium doped zinc oxide (IZO), antimony doped tin oxide (ATO), fluorine doped tin oxide (FTO). The anode may be formed into a composite electrode having a structure of e.g. ITO/Ag/ITO.

As the cathode, a low work function material is generally selected, so as to inject electrons smoothly into the organic functional layer 30 to combine with holes. Examples of the cathode materials include, but are not limited to, magnesium, calcium, sodium, potassium, titanium, indium, yttrium, lithium, gadolinium, aluminum, silver, tin and lead.

As a preferred embodiment, in the organic light emitting device of the present invention, the light emitting layer comprises the compound represented by Formula I. More preferably, the compound represented by Formula I is used as the host material or the guest material in the light emitting layer, and correspondingly, the guest material or the host material in the light emitting layer may be selected from the guest materials and the host material listed above.

In an embodiment, the organic material layer in the organic functional layer 30 may further comprise, in addition to the light emitting layer, a hole injection layer, a hole transporting layer, an electron transporting layer or an electron injection layer, and the hole injection layer, the hole transporting layer, the electron transporting layer and the electron injection layer may be made from materials known in the art. As a preferred embodiment, one or more of the hole injection layer, the hole transporting layer, the electron transporting layer and the electron injection layer comprise the compound represented by Formula I.

In an embodiment, the process for preparing the organic light emitting device comprises the following steps.

At S1, a substrate 10 is provided.

At S2, a first electrode 20 is formed on the substrate 10. The first electrode 20 may be formed by a method such as sputtering, vapor deposition, etc.

At S3, an organic functional layer 30 is formed on the first electrode 20. The organic functional layer 30 comprises one or more organic material layers, and at least one of the organic material layers is a light emitting layer, and at least one of the organic material layers in the organic functional layer 30 comprises the compound represented by Formula I.

The organic material layer in the organic functional layer 30 may be formed by a method such as spin coating, scrape coating, inkjet printing, silk-screen printing, etc. When the organic functional layer 30 comprises multiple organic material layers, said multiple organic material layers are formed sequentially in stacks by the above methods.

At S4, a second electrode 40 is formed on the organic functional layer 30, wherein the second electrode 40 may be formed by the same methods used for the first electrode 20.

The present invention further provides a process for preparing the compound represented by Formula I, and the starting materials used in said process are the compounds represented by the following Formula A and Formula B.

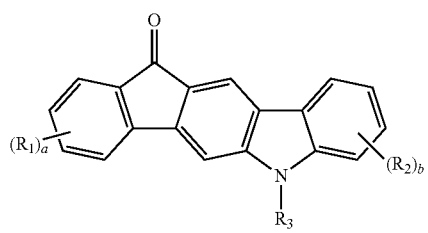

A

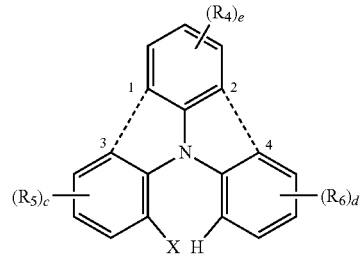

B

Said process comprises a step of nucleophilic reaction of a compound represented by Formula A and a compound represented by Formula B to produce the compound represented by Formula I. As an example, the nucleophilic reaction may be carried out in an ether solvent, such as anhydrous tetrahydrofuran, in the presence of n-BuLi, and tetrakis(triphenylphosphine)palladium.

In Formula A and Formula B, $R_1$ and $R_2$ are each independently hydrogen, halogen, trifluoromethyl, nitro or cyano, or have a structure of $(R_7)_f$—$R_8$—, a structure of

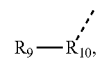

or a structure of

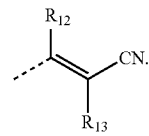

In the structure of $(R_7)_f$—$R_8$—, $R_8$ is C6~C34 aryl, or C3~C34 nitrogen-containing heteroaryl, and $R_7$ is hydrogen, halogen, trifluoromethyl, nitro or cyano, and f is an integer greater than or equal to 1, with an upper limit of f being 30.

In the structure of

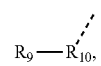

$R_{10}$ is

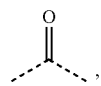

and $R_9$ is C1~C8 alkyl, C6~C12 aryl; or $R_{10}$ is

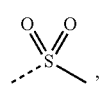

and $R_9$ is C6~C12 aryl; or $R_{10}$ is

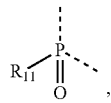

and $R_9$ and $R_{11}$ are each independently C6~C12 aryl.

In the structure of

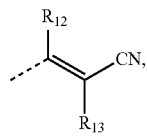

$R_{12}$ and $R_{13}$ are each independently hydrogen, C1~C8 alkyl, C6~C12 aryl.

$R_3$ has a structure of the above $(R_7)_f$—$R_8$—. $R_4$, $R_5$ and $R_6$ are each independently hydrogen, C1~C8 alkyl or heteroalkyl, C6~C8 aryl or C4~C8 heteroaryl.

In Formula B, the dashed line between the carbon atoms at position 1 and position 3 represents that a C—C bond may be present or not present between the two carbon atoms; and the dashed line between the carbon atoms at position 2 and position 4 represents that a C—C bond may be present or not present between the two carbon atoms.

a and b are each independently an integer of 1~4. c, d and e are each independently an integer of 1~3.

X is halogen, preferably bromine.

An "H" on the benzene ring in Formula B indicates said H atom is not substituted by $R_6$.

Next, the present invention will be illustrated in more details with reference to the Examples, but the present invention is not limited thereto, as long as the scope does not go beyond the spirit of the present invention. It shall be noted that the following Compounds 1, 2, 4 and 5 are the above compounds numbered 1, 2, 4 and 5.

Example 1

Synthesis of Compound 1

The synthesis of Compound 1 comprises the following steps.

Step 1: preparation of Compound A-1, the reaction scheme being as follows:

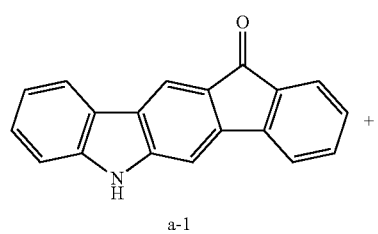

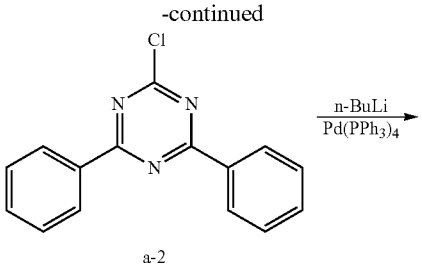

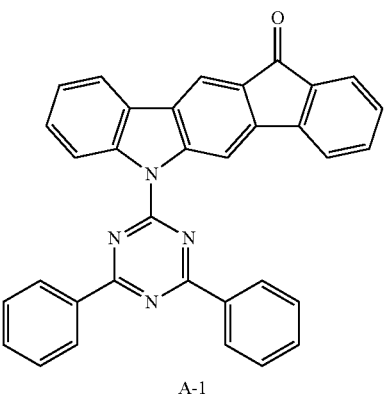

In a nitrogen atmosphere, 0.2 g (0.75 mmol) of indeno-carbazolone a-1 was added into 10 mL of anhydrous tetrahydrofuran, and stirred to dissolve. In an ice bath, 0.5 mL (0.8 mmol) of n-BuLi with a molar concentration of 1.6 mol/L was slowly added dropwise to the above tetrahydrofuran solution. After addition, the reaction was continued for 30 min to give a yellow suspension. 0.22 g (0.8 mmol) of 2-chloro-4,6-diphenyl-1,3,5-triazine a-2 and 0.04 g (0.04 mmol) of tetrakis(triphenylphosphine)palladium Pd(PPh$_3$)$_4$ were dissolved in 5 mL of tetrahydrofuran, and the tetrahydrofuran solution of 2-chloro-4,6-diphenyl-1,3,5-triazine a-2 and tetrakis(triphenylphosphine)palladium Pd(PPh$_3$)$_4$ was slowly added dropwise to the yellow suspension obtained above. The mixture was heated to 80° C. and reacted overnight. After the reaction was complete, the reaction system was cooled down to room temperature, and suctioned to give a white cake, which was washed with brine and then dried. The dried solid was recrystallized from 10 mL toluene to give 0.25 g of a white solid. Yield: 66%.

MALDI-TOF: m/z: 500.16. $^1$H NMR (400 MHz, CDCl$_3$): δ/ppm, 8.80 (s, 1H); 8.34-8.55 (m, 3H); 8.28 (m, 4H); 7.94 (d, 1H); 7.72-7.70 (m, 2H); 7.51 (m, 5H); 7.41 (m, 2H); 7.33-7.25 (m, 2H).

Step 2: Synthesis of Compound B-1:

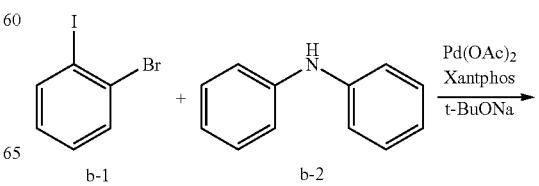

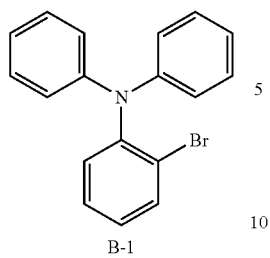

B-1

2.8 g (10 mmol) of 2-bromo iodobenzene b-1, 2 g (12 mmol) of diphenyl amine b-2, 1.4 g (15 mmol) of sodium tert-butoxide t-BuONa, 0.1 g (0.5 mmol) of palladium acetate Pd(OAc)₂ and 0.28 g (0.5 mmol) of 4,5-bis(diphenylphosphino)-9,9-dimethyl xanthene Xantphos were added into 30 mL of toluene. The toluene solution was heated to 100° C., and stirred at the same temperature for 12 h. After the reaction was complete, the reaction system was cooled down to room temperature, followed by addition of 100 mL of water to quench the reaction. The organic phase was then extracted with dichloromethane (90 mL). The solvent was removed by rotary evaporation. The product was purified with column chromatography (mobile phase: n-hexane:dichloromethane=19:1) to give 2.4 g of a pale yellow solid. Yield: 74%.

HRMS (ESI): m/z: 324.0407. ¹H NMR (400 MHz, CDCl₃): δ/ppm, 6.59-6.62 (m, 1H); 6.80-6.84 (m, 4H); 6.97-7.06 (m, 4H); 7.19-7.27 (m, 1H); 7.29-7.30 (m, 1H); 7.39-7.41 (m, 2H); 8.07-8.09 (m, 1H).

Step 3: Synthesis of Compound 1:

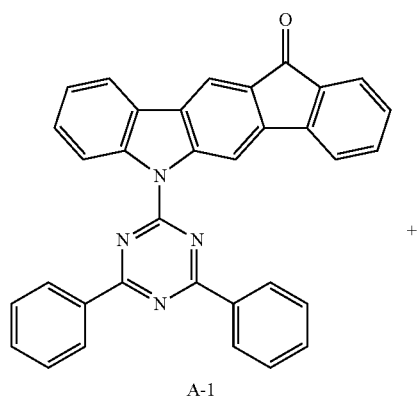

A-1

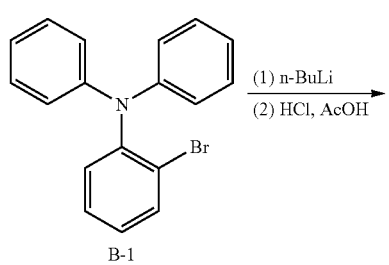

B-1

(1) n-BuLi
(2) HCl, AcOH

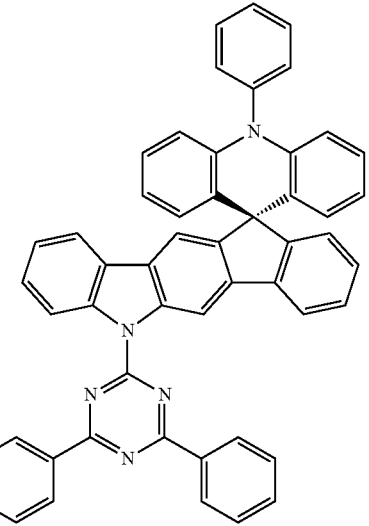

1

In a nitrogen atmosphere, 0.15 g (0.5 mmol) of B-1 was added into 10 mL of anhydrous tetrahydrofuran, and stirred to dissolve. The above tetrahydrofuran solution was cooled down to −78° C., to which was slowly added dropwise 0.3 mL (0.5 mmol) of n-BuLi with a molar concentration of 1.6 mol/L. After addition, the reaction was continued for 30 min. 0.2 g (0.4 mmol) of A-1 was dissolved in 5 mL of tetrahydrofuran, and the tetrahydrofuran solution of A-1 was slowly added dropwise to the above reaction system. After the addition, the mixture was naturally warmed up to room temperature, and reacted overnight at room temperature. After the reaction was complete, 100 mL of water was added to the reaction system to quench the reaction. The organic phase was then extracted with dichloromethane (90 mL). The solvent was removed by rotary evaporation. 10 mL of toluene was added to the reaction product obtained by removing solvent, stirred to wash, and suctioned to give a crude alcoholic intermediate, which was added into 5 mL of concentrated hydrochloric acid HCl and 50 mL of acetic acid AcOH. The mixed solution was heated to reflux and reacted for 2 h, followed by cooling the reaction system down to room temperature. 100 mL of water was added to the reaction system, followed by neutralizing with a saturated solution of sodium bicarbonate NaHCO₃. The organic phase was extracted with dichloromethane (30 m). The solvent was removed by rotary evaporation. The product was purified with column chromatography (mobile phase: n-hexane:dichloromethane=3:1) to give 0.17 g of a white solid. Yield: 51%.

MALDI-TOF: m/z: 727.27. ¹H NMR (400 MHz, CDCl₃): δ/ppm, 8.55 (d, 1H); 8.28 (m, 4H); 8.09-8.05 (m, 2H); 7.94 (d, 1H); 6.98 (d, 1H); 8.09-8.05 (m, 2H); 7.51-7.41 (m, 8H); 7.33-7.20 (m, 5H); 7.01-6.98 (m, 4H); 6.81 (m, 1H); 6.69-6.63 (m, 4H).

Compound 1 was synthesized from simplest starting materials with only 3 steps. Therefore, the synthesis route is simple and environment friendly, with a high yield and a low cost.

Test of the Energy Structure of Compound 1

The energy levels of the obtained Compound 1 were determined by quantum calculation, and the results are shown in Table 1. Specifically, the distribution of the frontier molecular orbitals of Compound 1 were optimized and calculated at the B3LYP/6-31G(d) calculation level using Gaussian 09 package (Gaussian Inc.) based on Time-Dependent Density Functional Theory (TDDFT), wherein a program developed by Frisch, M. J., Trucks, G. W., etc. in 2009 was used.

The calculations gave HOMO=−5.15 eV; and LUMO=−2.35 eV. It can be determined accordingly that, for Compound 1, the energy for exciting singlets, S1, is 2.35 eV, and that for exiting triplets, T1, is 2.18 eV, and the energy difference therebetween, $\Delta E_{ST}$, is 0.17 eV, which is less than 0.2 eV. Therefore, when Compound 1 is used as a luminescent material, RISC can be achieved, i.e., triplet excitons are converted to singlet excitons through reverse intersystem crossing to emit light.

Figure 2:
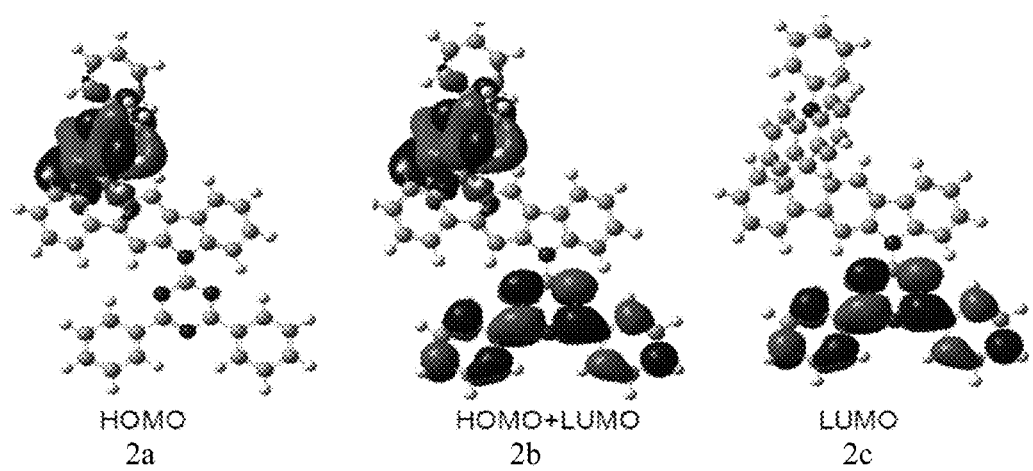

In addition, the inventors determined the distribution of the orbitals of Compound 1 through Gaussian simulated calculation based on the structure of the molecule. The following points can be seen from FIGS. 2a-2c.

1. Compound 1 generally comprises three moieties: indenocarbazole, triphenyl amine, and 4,6-diphenyl-1,3,5-triazine (i.e. $R_3$ in Formula I), wherein "indenocarbazole" is an intermediate bridging body, which is connected to the "triphenyl amine" moiety through an $SP^3$ hybridized C atom, and to the "$R_3$" moiety through an $SP^3$ hybridized N atom.

2. Almost all HOMOs are distributed on the "triphenyl amine" moiety, which means that the "triphenyl amine" moiety is the "donor unit" of the whole Compound 1 (electron donating group).

3. Almost all LUMOs are distributed on the "$R_3$" moiety, which means that $R_3$ (4,6-diphenyl-1,3,5-triazine) is the "receptor unit" of the whole Compound 1 (electron withdrawing group).

4. The "donor unit" and the "receptor unit" of Compound 1 are located on two different axes, since they are separated by two $SP^3$ hybridized atoms. The inventors brilliantly use "indenocarbazole" as a bridging body to achieve the double-axes design of the compound of the present invention, which can shorten the conjugation length, and improve the thermodynamic stability of the molecule. At the same time, by shortening the conjugation length, the transfer of excess intramolecular charges may be better avoided, and the light emitting spectrum can be narrowed. This can be proved by the distribution of the frontier molecular orbitals, in which HOMO and LUMO are completely separated, which restricts the transfer of excess intramolecular charges and narrows the spectrum, and at the same time reduces the energy for reverse crossing of triplet excitons to singlet, so as to improve the light emitting (or improve the efficiency of light emitting).

Test of the Photoluminescence Spectrum of Compound 1

Figure 3:
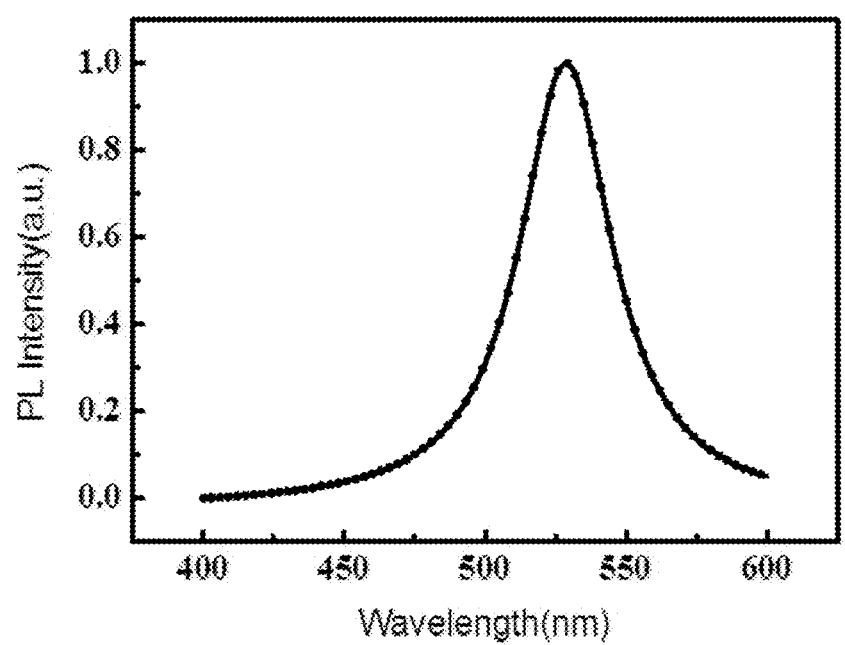
FIG. 3 shows the fluorescence emission spectrum of Compound 1 in Example 1 of the present invention in toluene.

Compound 1 was dissolved in toluene, and the fluorescence emission spectrum of Compound 1 was determined using a fluorescence spectrometer. See FIG. 3.

The fluorescence emission spectrum of Compound 1 is a single peak, and the peak value corresponds to a wavelength $\lambda_{em}$ of about 528 nm. Therefore, Compound 1 emits green fluorescence. In addition, it can be seen from FIG. 3 that the full width at half maximum in the fluorescence spectrum is 39 nm, which indicates a narrow fluorescence emission spectrum (this confirms from another point of view the above point 4), i.e. Compound 1 can avoid the transfer of excess intramolecular charges, and narrow the light emitting spectrum) and high color purity.

Furthermore, the radiation rate constant was calculated according to Einstein spontaneous radiation by referring to Table 1, and the fluorescence lifetime τ of Compound 1 was calculated to be about 10 μS, which is 3-order higher that the lifetime of traditional fluorescent materials, which indicates good effect of delayed fluorescence (generally speaking, τ above 1 μS means an effect of "delayed fluorescence").

Examples 2-4

The compounds obtained in Examples 2-4 correspond to the above Compounds 2, 4 and 5, respectively.

Compounds 2, 4 and 5 were synthesized following the three-step method of Example 1, and the detailed procedures are not repeated herein.

Figure 4:
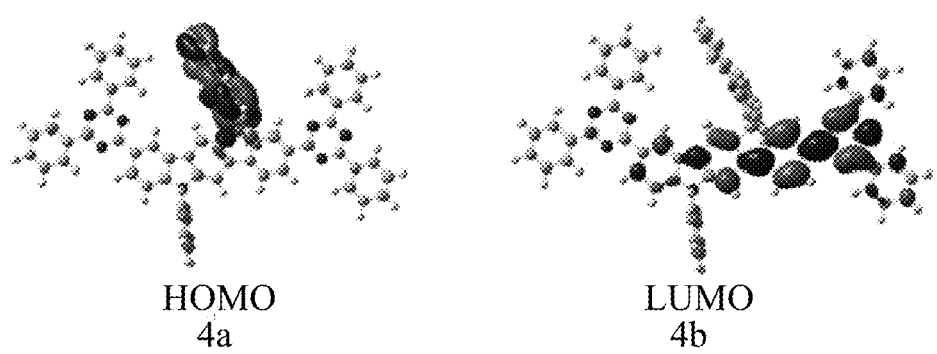
Figure 5:
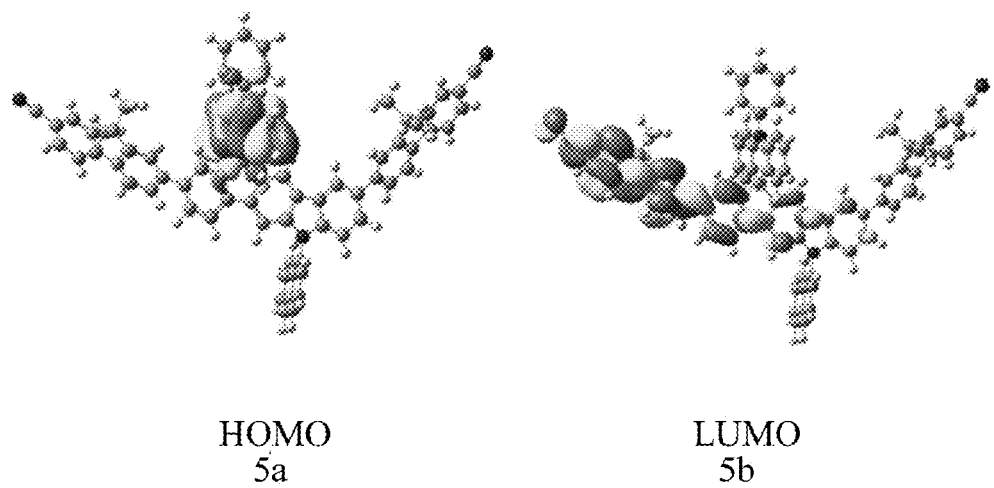
Figure 6:
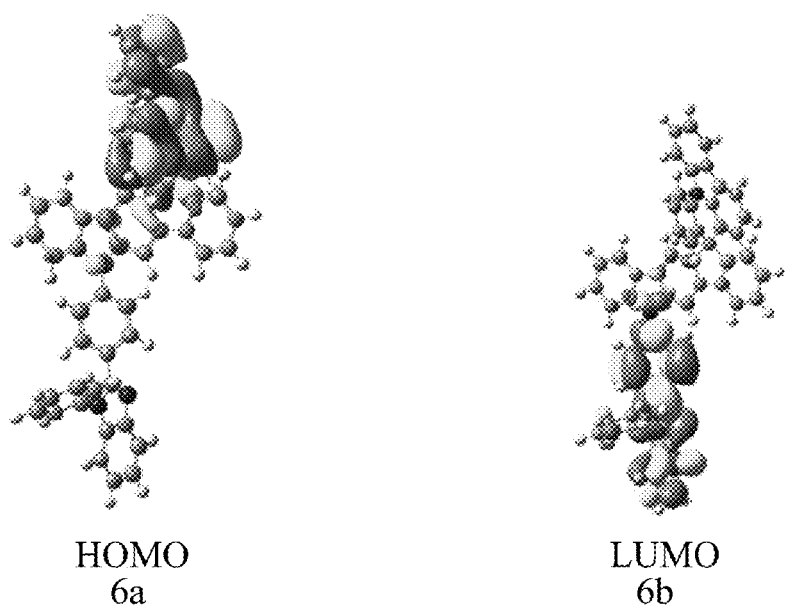

In order to better illustrate the effect of thermally activated delayed fluorescence of the compounds of the present invention, the energy structures of the compounds of Examples 2-4 were tested. In one aspect, the distributions of the orbitals of Compounds 2, 4 and 5 were determined through Gaussian simulated calculation based on the structures of the molecules. See FIGS. 4-6.

As can be seen from FIGS. 4a-6b, HOMOs and LUMOs of Compounds 2, 4 and 5 are separated through the bridging body "indenocarbazole".

In another aspect, the energy data of Compounds 2, 4 and 5 were determined by the simulated calculation described in Example 1. See the following Table 1.

TABLE 1

| Ex. | Comp. | HOMO (eV) | LUMO (eV) | $S_1$ (eV) | $T_1$ (eV) | $\Delta E_{ST}$ (eV) | Eg (eV) | τ (μS) |
|---|---|---|---|---|---|---|---|---|
| 1 | 1 | −5.15 | −2.35 | 2.35 | 2.18 | 0.17 | 2.8 | 10 |
| 2 | 2 | −5.32 | −2.53 | 2.48 | 2.29 | 0.18 | 2.79 | 2.6 |
| 3 | 4 | −5.07 | −2.49 | 2.28 | 2.17 | 0.11 | 2.58 | 6.9 |
| 4 | 5 | −5.18 | −2.30 | 2.52 | 2.36 | 0.16 | 2.88 | 5 |

In Table 1, HOMO represents highest occupied molecular orbital;
LUMO represents lowest unoccupied molecular orbital;
$S_1$ represents the energy for exciting singlets;
$T_1$ represents the energy for exciting triplets;
$\Delta E_{ST}$ represents the energy difference between the energies for exciting triplets and singlets;
Eg represents forbidden bandwidth; and
τ represents fluorescence lifetime.

As can be seen from Table 1, in Compounds 2, 4 and 5, the energy differences $\Delta E_{ST}$ between the energy for exciting singlets, S1, and that for exciting triplets, T1, are all less than 0.2 eV. Accordingly, when Compounds 2, 4 and 5 are used as luminescent materials, RISC can be achieved, i.e., triplet excitons are converted to singlet excitons through reverse intersystem crossing to emit light. The fluorescence lifetimes τ of Compounds 2, 4 and 5 calculated according to Einstein spontaneous radiation are all above 1 μS, which indicates good effect of delayed fluorescence. Specifically, by comparing Compound 2 with Compound 1, in both of which the receptor is diphenyl triazine, when the donor is changed from triphenyl amine to carbazole, the HOMO energy level of the molecule is further reduced. This is because carbazole has higher energy. This indirectly confirms that the strategy of energy band separation is successful. It can be seen by comparing Compounds 2 and 4 with Compounds 1 and 5 that, when the molecule is substituted with two donors, it has "deeper" LUMO. This is also consistent with expectation, since two donors further reduce the electron cloud density of the LUMO unit. Lower LUMO energy level of the light emitting layer is favorable for electron injection, which reduces the interface barrier and therefore reduces the voltage.

Application Example 1

This application example provides an organic light emitting device employing the above Compound 1. Referring to FIG. 1, the device comprises: a substrate 10, a first electrode 20 (anode) disposed on the substrate 10, a second electrode 40 (cathode) disposed opposite to the first electrode 20, an organic functional layer 30 disposed between the first electrode 20 and the second electrode 40, wherein the organic functional layer 30 comprises in sequence from above a hole injection layer, a hole transporting layer, a light emitting layer, an electron transporting layer and an electron injection layer.

In the light emitting layer material, the host material is CBP (4,4'-bis(N-carbazole)-1,1'-diphenyl), and the guest material is Compound 1 obtained in Example 1. Here, the light emitting layer material is a green fluorescent material.

The performances of the device were measured with Spectroscan PR 705 spectrometer and Keithley 236 current and voltage source measurement system, and the results are shown in Table 2.

TABLE 2

| Device | $V_{turn-on}$ [V] | $E_{L(max)}/E_{L(10\ mA/cm^2)}$ (cd A$^{-1}$) | $h_{p(max)}$ (lm W$^{-1}$) | $EQE_{(max)}$ (%) | CIE (x, y) |
|---|---|---|---|---|---|
| Appln. Ex. 1 | 2.4 | 20.95/19.7 | 26.2 | 4.75 | (0.23, 0.66) |

In Table 2, $V_{turn-on}$ represents turn-on voltage;
$E_{L(max)}$ represents maximum current efficiency;
$E_{L(10\ mA/cm^2)}$ represents current efficiency at a current density of 10 mA/cm$^2$;
$h_{p(max)}$ represents power efficiency;
$EQE_{(max)}$ represents external quantum efficiency; and
CIE (x, y) represents chromaticity coordinate.

As can be seen from Table 2, the external quantum efficiency (EQE) of the device approaches the limit of a fluorescence device (5%). Meanwhile, the turn-on voltage ($V_{turn-on}$) is extremely low, which is favorable for reducing power consumption. The bottom emitting chromaticity coordinate (0.23, 0.66) is very close to the coordinate for standard green light (0.23, 0.71). The performances of the above organic light emitting device are mainly derived from the fact that Compound 1 in the light emitting layer has relatively narrow fluorescence spectrum, relatively long fluorescence lifetime and relatively small singlet-triplet energy level difference.

Application Example 2

However, the application examples of the present invention are not limited to Application Example 1. For example, the light emitting layer material may employ Compound 1 as the host material, and a compound emitting red fluorescence as the guest material. Specifically, the guest material may be 4-(dicyanomethylene)-2-t-butyl-6-(1,1,7,7-tetramethyl-julolidyl-4-vinyl)-4H-pyran (DCJTB). Here, the light emitting layer material is a red fluorescent material.

The performances of the device were measured with Spectroscan PR 705 spectrometer and Keithley 236 current and voltage source measurement system, and the results are shown in Table 3.

TABLE 3

| Device | $V_{turn-on}$ [V] | $E_{L(max)}/E_{L(10\ mA/cm^2)}$ (cd A$^{-1}$) | $h_{p(max)}$ (lm W$^{-1}$) | $EQE_{(max)}$ (%) | CIE (x, y) |
|---|---|---|---|---|---|
| Appln. Ex. 2 | 2.2 | 12.92/12.4 | 16.1 | 6.12 | (0.63, 0.37) |

In Table 3, $V_{turn-on}$ represents turn-on voltage;
$E_{L(max)}$ represents maximum current efficiency;
$E_{L(10\ mA/cm^2)}$ represents current efficiency at a current density of 10 mA/cm$^2$;
$h_{p(max)}$ represents power efficiency;
$EQE_{(max)}$ represents external quantum efficiency; and
CIE (x, y) represents chromaticity coordinate.

As can be seen from Table 3, the efficiency of the device exceeds the limit of a fluorescence device (5%), i.e. significantly higher than the efficiency of traditional fluorescence devices. Meanwhile, the turn-on voltage ($V_{turn-on}$) is extremely low, which is favorable for reducing power consumption. The bottom emitting chromaticity coordinate (0.63, 0.37) is very close to the coordinate for standard red light (0.67, 0.33).

Although preferred embodiments of the present invention are described herein, these embodiments are provided only for illustration. It should be understood that variants of the embodiments of the present invention described herein may also be used to implement the present invention. It should be understood by a person with ordinary skill in the art that there might be various variants, modifications and substitutions without departing from the scope of the present invention. It should be understood that the scopes for protection of the various aspects of the present invention depend on the Claims, and the methods and structures within the scope of the Claims and equivalent methods and structures are all encompassed by the Claims.

What is claimed is:

1. A luminescent material, comprising a compound represented by the following Formula I,

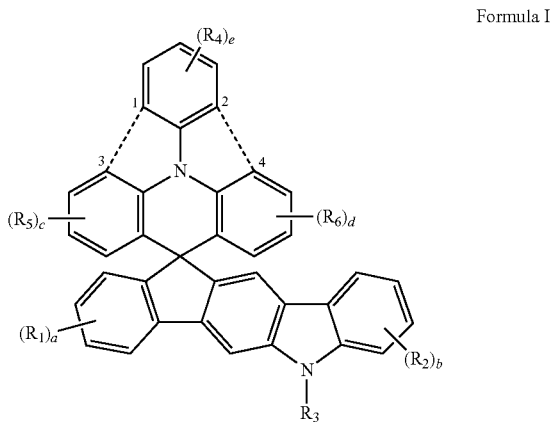

Formula I wherein R₁ and R₂ each independently have a structure of $(R_7)_f$—R₈;

R₃ has a structure of $(R_7)_f$—R₈—;

in the structure of $(R_7)_f$—R₈—;

R₈ is C6~C34 aryl or C3~C34 nitrogen-containing heteroaryl, and R₇ is hydrogen, halogen, trifluoromethyl, nitro or cyano, and f is an integer greater than or equal to 1;

R₄, R₅ and R₆ are each independently hydrogen, C1~C8 alkyl or heteroalkyl, C6~C8 aryl or C4~C8 heteroaryl;

in Formula I, the dashed line between the carbon atoms at position 1 and position 3 represents that a C—C bond may be present or not present between the two carbon atoms;

in Formula I, the dashed line between the carbon atoms at position 2 and position 4 represents that a C—C bond may be present or not present between the two carbon atoms;

a and b are each independently an integer of 1~4; c, d and e are each independently an integer of 1~3, wherein the compound is used as a guest material in the luminescent material, the luminescent material further comprising a host material which is selected from the following compounds:

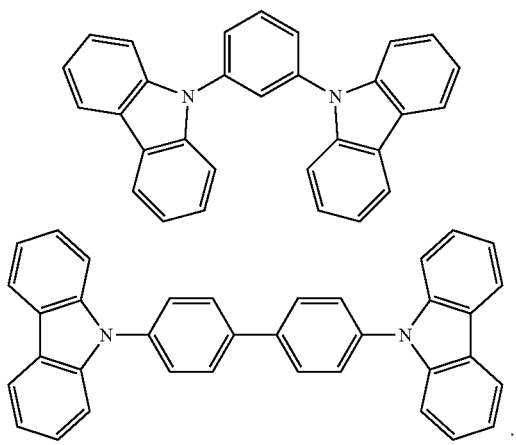

2. The luminescent material according to claim 1, wherein in the structure of $(R_7)_f$—R₈—, R₈ is selected from the group consisting of phenyl, biphenyl, naphthyl, fluorenyl, pyridyl, pyrimidyl, and isoquinolinyl, or R₈ has a structure of

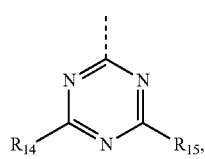

wherein R₁₄ and R₁₅ are each independently phenyl, naphthyl or anthryl.

3. The luminescent material according to claim 1, wherein R₃ is selected from the group consisting of:

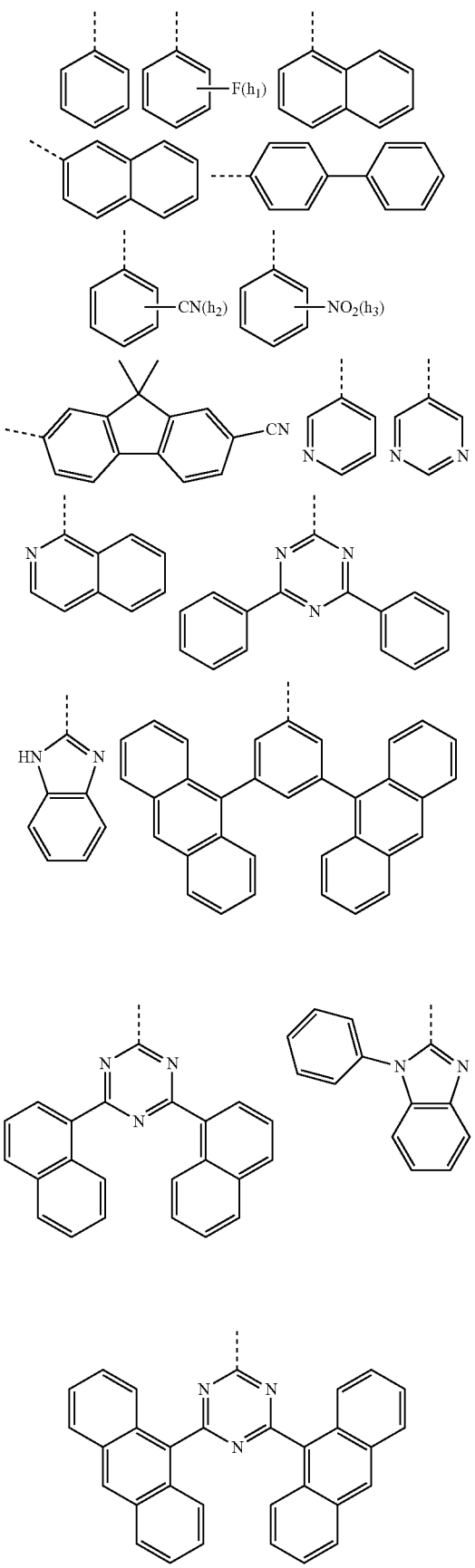

39

-continued

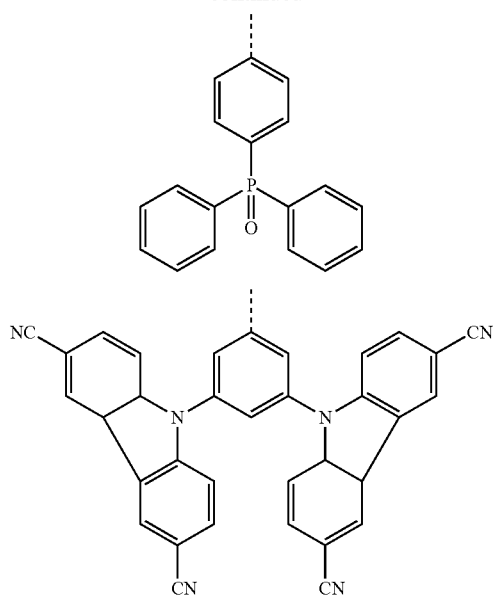

wherein $h_1$, $h_2$ and $h_3$ are each independently an integer of 1~5.

4. The luminescent material according to claim 1, wherein the compound has a structure represented by any one of the following Formulae II to IV, Formula II

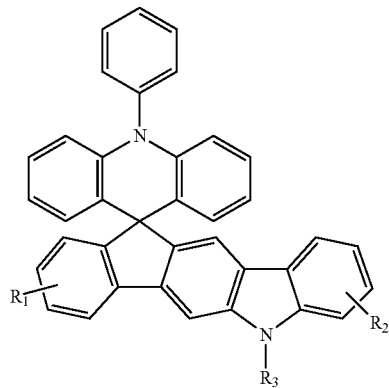

Formula III

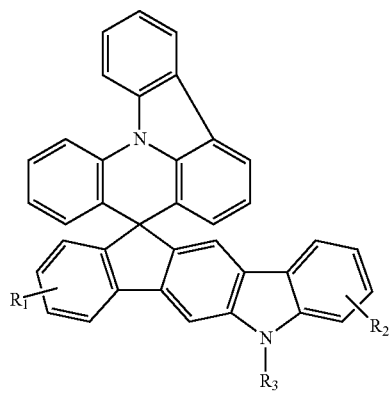

40

-continued

Formula IV

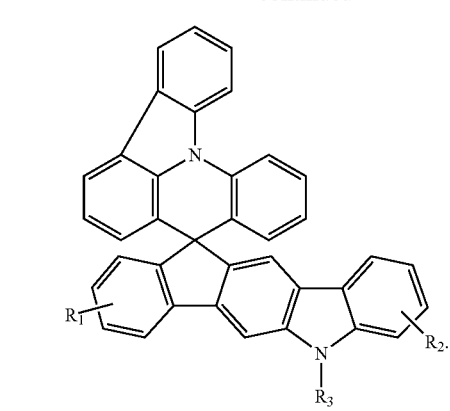

5. An organic light emitting device, comprising:
a substrate;
a first electrode disposed on the substrate;
a second electrode disposed opposite to the first electrode; and
an organic functional layer disposed between the first electrode and the second electrode, the organic functional layer comprising one or more organic material layers, and at least one of the organic material layers being light emitting layer;
wherein at least one of the organic material layers in the organic functional layer comprises a compound represented by the following Formula I, Formula I

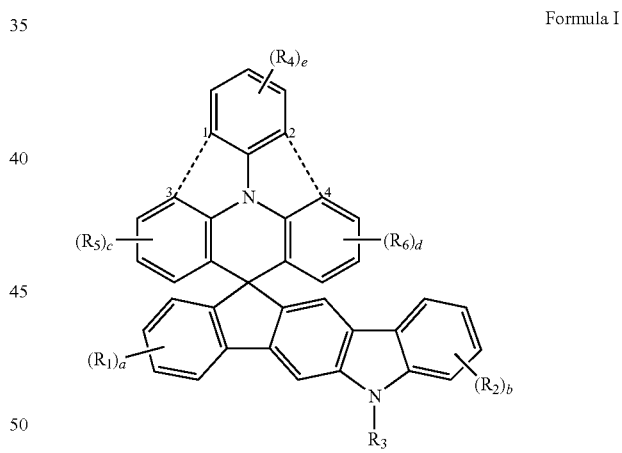

wherein $R_1$ and $R_2$ each independently have a structure of $(R_7)_f$—$R_8$—;
$R_3$ has a structure of $(R_7)_f$—$R_8$—;
in the structure of $(R_7)_f$—$R_8$—,
$R_8$ is C6~C34 aryl or C3~C34 nitrogen-containing heteroaryl, and $R_7$ is hydrogen, halogen, trifluoromethyl, nitro or cyano, and f is an integer greater than or equal to 1;
$R_4$, $R_5$ and $R_6$ are each independently hydrogen, C1~C8 alkyl or heteroalkyl, C6~C8 aryl or C4~C8 heteroaryl;
in Formula I, the dashed line between the carbon atoms at position 1 and position 3 represents that a C—C bond may be present or not present between the two carbon atoms;

in Formula I, the dashed line between the carbon atoms at position 2 and position 4 represents that a C—C bond may be present or not present between the two carbon atoms;

a and b are each independently an integer of 1~4; c, d and e are each independently an integer of 1~3, wherein the compound is used as a guest material in the luminescent material, the luminescent material further comprising a host material which is selected from the following compounds:

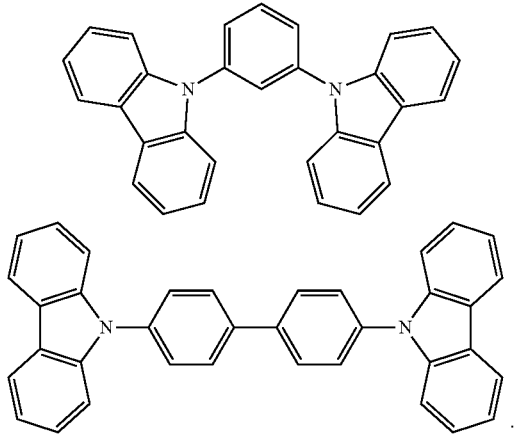

6. The organic light emitting device according to claim 5, wherein in the structure of $(R_7)_f$—$R_8$—, $R_8$ is selected from the group consisting of phenyl, biphenyl, naphthyl, fluorenyl, pyridyl, pyrimidyl, and isoquinolinyl, or $R_8$ has a structure of

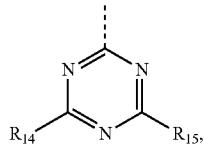

wherein $R_{14}$ and $R_{15}$ are each independently phenyl, naphthyl or anthryl.

7. The organic light emitting device according to claim 5, wherein $R_3$ is selected from the group consisting of:

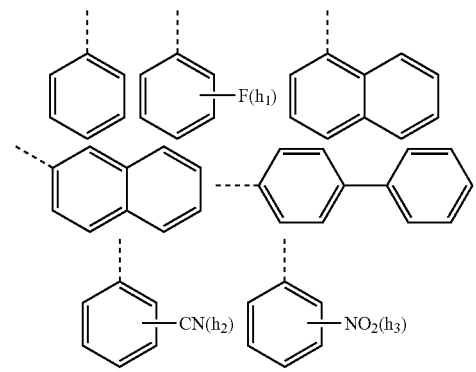

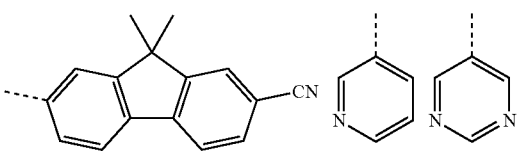

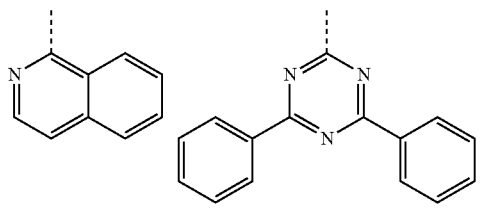

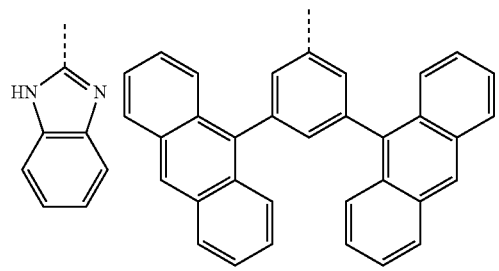

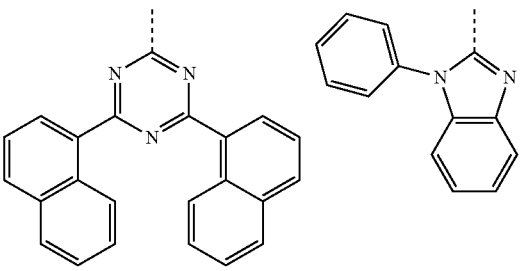

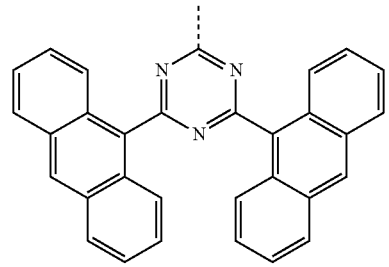

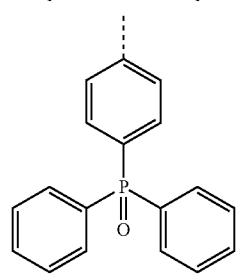

-continued

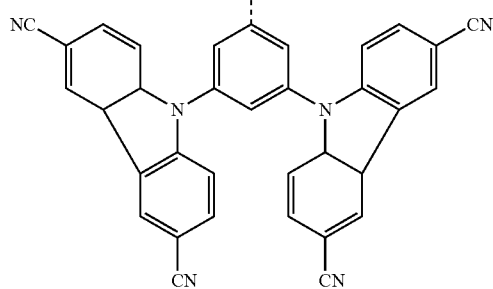

wherein $h_1$, $h_2$ and $h_3$ are each independently an integer of 1~5.

8. The organic light emitting device according to claim 5, wherein the compound has a structure represented by any one of the following Formulae II to IV, Formula II

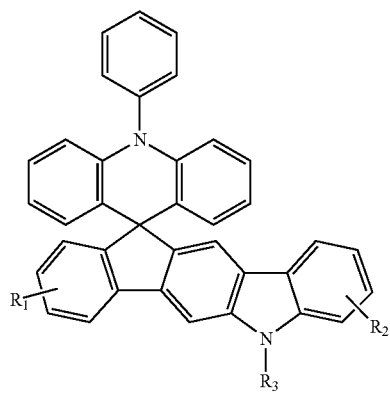

-continued

Formula III

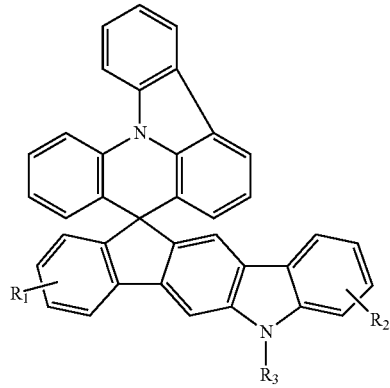

Formula IV

9. The organic light emitting device according to claim 5, wherein the light emitting layer comprises the compound represented by Formula I.

* * * * *